United States Patent

Muller et al.

Patent Number: 5,889,045
Date of Patent: Mar. 30, 1999

[54] BENZOPYRAN COMPOUNDS

[75] Inventors: Timothée Muller, La Chapelle Basse Mer; Claudie Moulin, Pace; Muriel Duflos, Vue; Sylvie Robert-Piessard, Nantes; Guillaume Le Baut, Saint Sebastien sur Loire; Alain Tonnerre, Bouguenais; Daniel-Henri Caignard, Le Pecq; Dominique Manechez, Puteaux; Pierre Renard, Versailles, all of France

[73] Assignee: Adir et Compagnie, Courbevoie, France

[21] Appl. No.: 977,793

[22] Filed: Nov. 25, 1997

[30] Foreign Application Priority Data

Nov. 26, 1996 [FR] France ................ 96 14470

[51] Int. Cl.[6] ............ A61K 31/355; A61K 31/47; C07D 311/04; C07D 215/36
[52] U.S. Cl. ............ 514/458; 514/456; 514/314; 514/269; 549/405; 549/407; 546/172; 544/333
[58] Field of Search ............ 549/405, 407; 514/456, 458, 314, 269; 546/172; 544/333

[56] References Cited

U.S. PATENT DOCUMENTS

| | | | |
|---|---|---|---|
| 5,236,935 | 8/1993 | Yoo et al. | 514/337 |
| 5,300,511 | 4/1994 | Yoo et al. | 514/278 |
| 5,310,753 | 5/1994 | Englert et al. | 514/422 |
| 5,574,061 | 11/1996 | Shiota et al. | 514/456 |
| 5,646,308 | 7/1997 | Koga et al. | 549/404 |
| 5,703,118 | 12/1997 | Durand et al. | 514/456 |
| 5,767,132 | 6/1998 | Bottcher et al. | 514/337 |
| 5,811,448 | 9/1998 | Englert et al. | 514/422 |

*Primary Examiner*—Deborah G. Lambkin
*Attorney, Agent, or Firm*—The Firm of Gordon W. Hueschen

[57] ABSTRACT

A compound of formula (I):

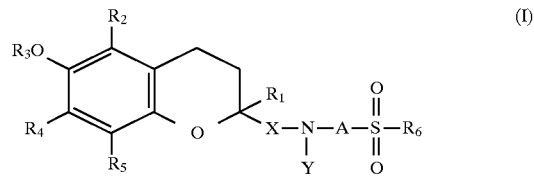

in which:

$R_1$ represents alkyl, $R_2$, $R_4$ and $R_5$, which may be identical or different, represent hydrogen or alkyl, $R_3$ represents any one of the groups as defined in the description, X represents carbonyl or methylene, Y represents hydrogen or alkyl or aryl, A represents single bond or alkylphenyl, $R_6$ represents any one of the groups as defined in the description, its isomers as well as its addition salts with a pharmaceutically acceptable acid or base, and medicinal productes containing the same are useful in the treatment of diabetes and complications of diabetic disease.

10 Claims, No Drawings

BENZOPYRAN COMPOUNDS

FIELD OF THE INVENTION

The present invention relates to novel benzopyran derivatives.

More specifically, the invention relates to N-sulfonylbenzopyran-2-carboxamides and derivatives thereof, which is a family that has never been described to date to our knowledge.

The applicant has discovered that these compounds are therapeutically particularly advantageous in the treatment of diabetes, as well as in the treatment of the side effects of diabetic disease.

DETAILED DESCRIPTION OF THE INVENTION

More specifically, the present invention relates to compounds of general formula (I):

(I)

in which:
- $R_1$ represents a linear or branched ($C_1-C_9$) alkyl group;
- $R_2$, $R_4$ and $R_5$, which may be identical or different, each represent, independently of each other, a hydrogen atom or a linear or branched ($C_1-C_9$) alkyl group;
- $R_3$ represents a hydrogen atom, a linear or branched ($C_1-C_9$) alkyl group, a linear or branched ($C_1-C_9$) acyl group, a linear or branched carboxy ($C_1-C_9$) alkyl group, a linear or branched ($C_1-C_9$) alkoxycarbonyl group or a group which is optionally substituted with a halogen in position 7;
- X represents a carbonyl group or a methylene group;
- Y represents a hydrogen atom, a linear or branched ($C_1-C_9$) alkyl group or an optionally substituted aryl group;
- A represents
  either a single bond and, in this case:
    $R_6$ represents a linear or branched ($C_1-C_9$) alkyl group (optionally substituted with an aryl group which is itself optionally substituted), or an optionally substituted aryl group;
  or an alkylphenyl group (optionally substituted on the phenyl) —$R_b$—

$$-\underset{Y}{\underset{|}{N}}-$$

linear or branched ($C_1-C_9$) alkyl part $R_b$ being attached to the group and, in this case:
$R_6$ represents:
  an isocyanate group,
  an amino group optionally substituted with one or two identical or different, linear or branched ($C_1-C_9$) alkyl groups, or with a linear or branched ($C_1-C_9$) alkoxycarbonyl group,
  or a substituted urea group -NH-CO-NH-$R_7$ with $R_7$ representing a phenyl group (optionally substituted), a cyclo ($C_5-C_8$) alkyl group (optionally substituted with a linear or branched ($C_1-C_9$) alkyl group), or a 3-azabicyclo[3.3.0]octyl group, their isomers as well as their addition salts with a pharmaceutically acceptable acid or base.

Among the pharmaceutically acceptable acids, there may be mentioned, with no limitation being implied, hydrochloric acid, hydrobromic, sulfuric, tartaric, maleic, fumaric, oxalic, methanesulfonic, camphoric, ethanesulfonic, citric, phosphonic, acetic, trifluoroacetic, lactic, pyruvic, malonic, succinic, glutaric, ascorbic, and the like.

Among the pharmaceutically acceptable bases, there may be mentioned, with no limitation being implied, sodium hydroxide, potassium hydroxide, calcium hydroxide, sodium carbonate, potassium carbonate, calcium carbonate, triethylamine, diethylamine, ethanolamine, and the like.

The term aryl group is understood to refer to a phenyl or naphthyl group and the term substituted aryl group or substituted phenyl group is understood to refer to a substitution with 1 to 3 groups, which may be identical or different, chosen, independently of each other, from:
- linear or branched ($C_1-C_9$) alkyl,
- linear or branched ($C_1-C_9$) alkoxy,
- linear or branched ($C_1-C_9$) alkoxycarbonyl,
- carboxyl,
- linear or branched carboxy ($C_1-C_9$) alkyl,
- linear or branched ($C_1-C_9$) acyl,
- linear or branched ($C_1-C_9$) alkylcarbonylamino,
- linear or branched ($C_1-C_9$) aminoalkyl, where n is between 1 and 6 inclusive,
- amino optionally substituted with one or two identical or different, linear or branched ($C_1-C_9$) alkyl groups,
- linear or branched ($C_1-C_9$) alkenyl,
- nitro,
- halo,
- trihalomethyl,
- linear or branched phthalimido ($C_1-C_9$) alkyl.

The preferred compounds according to the invention are those for which:
- $R_1$, $R_2$, $R_4$ and $R_5$, which may be identical or different, represent a linear or branched ($C_1-C_9$) alkyl group,
- $R_3$ represents a hydrogen atom or a linear or branched ($C_1-C_9$) acyl group,
- X represents a carbonyl group,
- Y represents a hydrogen atom or a linear or branched ($C_1-C_9$) alkyl group and preferably a hydrogen atom,
- A represents
  a single bond and, in this case, $R_6$ advantageously represents an optionally substituted aryl group,
  or a phenylethyl group and, in this case, $R_6$ advantageously represents a substituted urea —NH—CO—NH—$R_7$ in which $R_7$ is as defined above, and, where appropriate, their isomers as well as their addition salts with a pharmaceutically acceptable acid or base.

In a particularly advantageous manner, the preferred compounds according to the invention are those for which A represents a single bond and $R_6$ represents a phenyl group substituted with a linear or branched ($C_1$–$C_9$) alkyl group, a halogen or a group

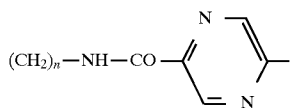

where n is between 1 and 6 inclusive.

The present invention relates more specifically to the compounds of fomula (I) which are 4-Chloro, 4-Bromo and 4-Methyl-N-(6-acetoxy-3,4-dihydro-2,5,7,8-tetramethyl-2H-1-benzopyran-2-carbonyl)-benzensulfonamide, their isomers as well as their addition salts with a pharmaceutically acceptable acide or base.

The invention also extends to the process for the preparation of the compounds of formula (I), wherein the starting material used is a compound of formula (II):

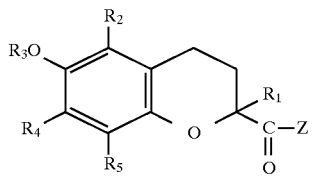

which:

Z represents a hydroxyl group or a halogen atom and $R_1$, $R_2$, $R_3$, $R_4$ and $R_5$ have the same meaning as in formula (I), which is condensed:

either, when A in formula (I) represents a single bond, with a compound of formula (III):

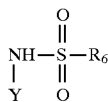

in which Y and $R_6$ have the same meaning as in formula (I), in order to give the compound of formula (I/a), a specific case of the compounds of formula (I):

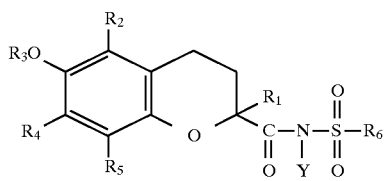

in which $R_1$, $R_2$, $R_3$, $R_4$, $R_5$, $R_6$ and Y have the same meaning as in formula (I), compound of formula (I/a) where the carbonyl function is reduced, if so desired, in order to give the compound of formula (I/b), a specific case of the compounds of formula (I):

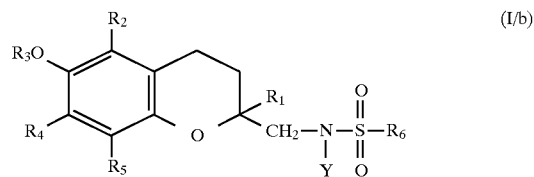

in which $R_1$, $R_2$, $R_3$, $R_4$, $R_5$, $R_6$ and Y have the same meaning as above (I), or, when A in formula (I) represents an alkylphenyl group —$R_b$—Ph, with a compound of formula (IV):

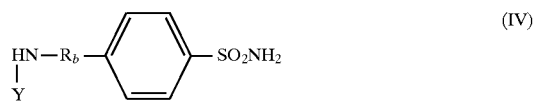

in which Y and $R_b$ have the same meaning as in formula (I), in order to give a mixture of two compounds of formulae (I/c) and (I/d) respectively, specific cases of compounds of formula (I)

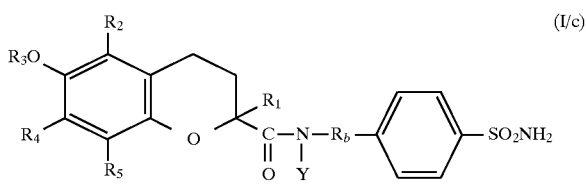

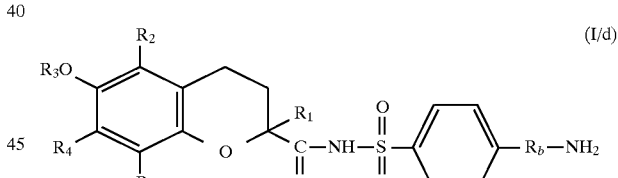

in which formulae (I/c) and (I/d) $R_b$, $R_1$, $R_2$, $R_3$, $R_4$, $R_5$ and Y have the same meaning as in formula (I), mixture from wich there is isolated, according to standard chromatography processes, compound of formula (I/c), wich is treated with phosgene in order to give the compound of formula (I/e), a specific case of the compounds of formula (I):

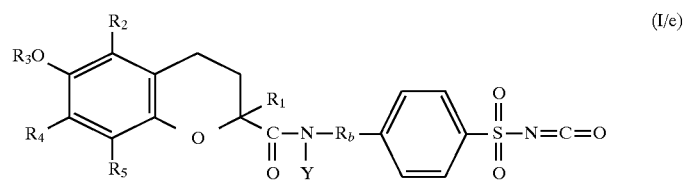

in which $R_b$, $R_1$, $R_2$, $R_3$, $R_4$, $R_5$ and Y have the same meaning as in formula (I),
which compound of formula (I/e) is treated with a compound of formula (V):

in which $R_7$ has the same meaning as in the general definition of formula (I),
in order to give the compounds of formula (I/f), a specific case of compounds of formula (I)

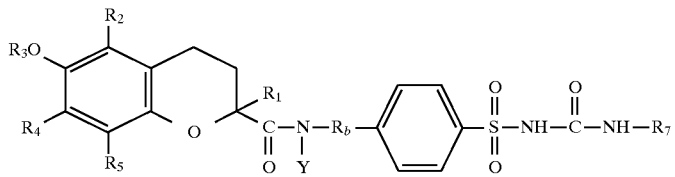

in which $R_b$, $R_1$, $R_2$, $R_3$, $R_4$, $R_5$, $R_7$ and Y have the same meaning as that presented in the general description of formula (I),
which compounds of formula (I/a) to (I/f) are purified, where appropriate, according to a standard purification technique, whose isomers are optionally separated according to a standard separation technique, and which are converted, if so desired, into the addition salts thereof with a pharmaceutically acceptable acid or base.

The compounds of formula (I) have advantageous pharmacological properties. In particular, they have the property of opposing the increase in glycemia in animals made artificially diabetic after loading with glucose and, in this respect, they are advantageous in the treatment of diabetic disease.

Furthermore, they have shown good antioxidant properties and, in this respect, are advantageous in the treatment of complications of diabetic disease due to micro- or macroangiopathies which entail nephropathy, neuropathy and retinopathies.

The compounds of the invention are also relatively nontoxic.

The subject of the present invention is also pharmaceutical compositions containing, as active principle, at least one compound of general formula (I) or one of the addition salts thereof with a pharmaceutically acceptable acid or, where appropriate, with a pharmaceutically acceptable base, alone or in combination with one or more inert, nontoxic excipients or vehicles.

Among the pharmaceutical compositions according to the invention, mention may be made more particularly of those which are suitable for oral, parenteral (intravenous or subcutaneous) or nasal administration, simple or sugar-coated tablets, sublingual tablets, sachets, packets, gelatin capsules, glossettes, lozenges, suppositories, creams, ointments, dermal gels, injectable preparations, drinkable suspensions, etc.

The dosage varies depending on the patient's age and weight, the nature and severity of the complaint and the route of administration. The latter may be oral, nasal, rectal or parenteral.

In general, the unit dosage ranges between 0.05 mg and 500 mg taken one to three times per 24 hours.

The examples which follow illustrate the invention but do not limit it in any way. The starting materials used are known products or are prepared according to known procedures.

The $^1$H nuclear magnetic resonance spectra were acquired using TMS (tetramethylsilane) as internal reference. The chemical shifts are expressed in parts per million (ppm). The infrared spectra were acquired in the form of potassium bromide discs containing about 1% of the product to be analyzed.

EXAMPLE 1

N-(6-Acetoxy-3,4-dihydro-2,5,7,8-tetramethyl-2H-1-benzopyran-2-carbonyl)-methanesulfonamide Method 1:

A mixture of 1.5 g of acetylated Trolox, or 6-acetoxy-3,4-dihydro-2,5,7,8-tetramethyl-2H-1-benzopyran-2-carboxylic acid, (5.13 mmol), 0.52 g (5.4 mmol) of methanesulfonamide, 0.66 g (5.4 mmol) of 4-dimethylaminopyridine and 0.84 ml (5.4 mmol) of N,N'-diisopropylcarbodiimide is dissolved in 90 ml of anhydrous dichloromethane. The mixture is stirred at room temperature for 18 hours.

The urea which has partially precipitated is filtered off. The filtrate is concentrated, left to cool and the urea is again filtered off. The operation is repeated once or twice more. The final filtrate is poured into 1M hydrochloric acid solution, the aqueous phase is extracted with dichloromethane and the organic phase is washed with saturated NaCl solution. The filtrate is dried over anhydrous sodium sulfate and the solvent is evaporated off. The product is precipitated from diisopropyl ether, filtered off and washed with ethanol in order to remove the traces of urea. The product is recrystallized from diisopropyl ether in order to collect 1.38 g of a white powder.

Yield: 73%
Melting point: 188° C. (diisopropyl ether)
$C_{17}H_{23}NO_6S$
Mr: 369.44
IR (KBr), $\nu$ cm$^{-1}$: 3360 ($\nu$NH); 1735 ($\nu$C=O ester); 1715 ($\nu$C=O amide); 1340 ($\nu$SO$_2$s);
1220 (com NH/CN); 1170 ($\nu$SO$_2$as).

EXAMPLE 2

4-Fluoro-N-(6-acetoxy-3,4-dihydro-2,5,7,8-tetramethyl-2H-1-benzopyran-2-carbonyl)benzene-sulfonamide The process is performed as in Method 1, using 4-fluorobenzenesulfonamide as reagent instead of methanesulfonamide.
Melting point: 130° C.

EXAMPLE 3

4-Chloro-N-(6-acetoxy-3,4-dihydro-2,5,7,8-tetramethyl-2H-1-benzopyran-2-carbonyl)benzenesulfonamide The process is performed as in Method 1, using 4-chlorobenzenesulfonamide as reagent instead of methanesulfonamide.
Melting point: 173° C.

EXAMPLE 4

4-Bromo-N-(6-acetoxy-3,4-dihydro-2,5,7,8-tetramethyl-2H-1-benzopyran-2-carbonyl)benzenesulfonamide The process is performed as in Method 1, using 4-bromobenzenesulfonamide as reagent instead of methanesulfonamide.
Melting point: 153°–155° C.

EXAMPLE 5

2-Methyl-N-(6-acetoxy-3,4-dihydro-2,5,7,8-tetramethyl-2H-1-benzopyran-2-carbonyl)benzenesulfonamide The process is performed as in Method 1, using 2-methylbenzenesulfonamide as reagent instead of methanesulfonamide.
Melting point: 165°–167° C.

EXAMPLE 6

N-(6-Acetoxy-3,4-dihydro-2,5,7,8-tetramethyl-2H-1-benzopyran-2-carbonyl)benzenesulfonamide The process is performed as in Method 1, using benzenesulfonamide as reagent instead of methanesulfonamide.
Melting point: 150° C.

EXAMPLE 7

4-Methoxycarbonyl-N-(6-acetoxy-3,4-dihydro-2,5,7,8-tetramethyl-2H-1-benzopyran-2-carbonyl)benzenesulfonamide The process is performed as in Method 1, using 4-methoxycarbonylbenzenesulfonamide as reagent instead of methanesulfonamide.
Melting point: 185° C.

EXAMPLE 8

N-(6-Acetoxy-3,4-dihydro-2,5,7,8-tetramethyl-2H-1-benzopyran-2-carbonyl)-2-naphthalenesulfonamide The process is performed as in Method 1, using 2-naphthalenesulfonamide as reagent instead of methanesulfonamide.
Melting point: 183° C.

EXAMPLE 9

N-(6-Acetoxy-3,4-dihydro-2,5,7,8-tetramethyl-2H-1-benzopyran-2-carbonyl)-1-naphthalenesulfonamide The process is performed as in Method 1, using 1-naphthalenesulfonamide as reagent instead of methanesulfonamide.
Melting point: 167°–169° C.

EXAMPLE 10

4-Isopropyl-N-(6-acetoxy-3,4-dihydro-2,5,7,8-tetramethyl-2H-1-benzopyran-2-carbonyl)benzene-sulfonamide
Method 2:

A solution of 2 g (6.84 mmol) of acetylated Trolox in 17 ml of anhydrous tetrahydrofuran is added dropwise to a stirred solution of 1.1 g (6.85 mmol) of carbonyidiimidazole in 13 ml of anhydrous tetrahydrofuran under nitrogen. The mixture is stirred for thirty minutes at room temperature and is then refluxed for thirty minutes. It is allowed to cool to room temperature. 1.36 g (6.85 mmol) of 4-isopropylbenzenesulfonamide are added and the mixture is stirred for 10 minutes. A solution of 1.03 ml (6.85 mmol) of DBU, or 1,8-diazabicyclo[5.4.0]undec-7-ene, in 6 ml of anhydrous THF are added dropwise. The mixture is stirred overnight at room temperature. The solvent is evaporated off. The residue is taken up in dichloromethane and washed with 1M aqueous hydrochloric acid solution and then with saturated aqueous sodium chloride solution. It is dried over anhydrous sodium sulfate. The solvent is evaporated off. The oil obtained is purified by chromatography on silica gel, eluting with a dichloromethane/ethanol mixture (99/1). Recrystallization of the product from diisopropyl ether gives 2.61 g of a white powder.
Yield: 78%
Melting point: 124°–126° C. (diisopropyl ether)
$C_{25}H_{31}NO_6S$
Mr: 489.59
IR (KBr), ν cm$^{-1}$: 3346 (νNH); 1766 (νC=O ester); 1726 (νC=O amide); 1597 (δNH); 1338 (νSO$_2$s); 1204 (comb NH/CN); 1081 (νSO$_2$as)

EXAMPLE 11

4-Ethyl-N-(6-acetoxy-3,4-dihydro-2,5,7,8-tetramethyl-2H-1-benzopyran-2-carbonyl)benzenesulfonamide The process is performed as in Method 2, using 4-ethylbenzenesulfonamide as reagent.
Melting point: 130° C.

EXAMPLE 12

3-Methyl-N-(6-acetoxy-3,4-dihydro-2,5,7,8-tetramethyl-2H-1-benzopyran-2-carbonyl)benzenesulfonamide The process is performed as in Method 2, using 3-methylbenzenesulfonamide as reagent.
Melting point: 89°–91° C.

EXAMPLE 13

2-Nitro-N-(6-acetoxy-3,4-dihydro-2,5,7,8-tetramethyl-2H-1-benzopyran-2-carbonyl)benzenesulfonamide The process is performed as in Method 2, using 2-nitrobenzenesulfonamide as reagent.
Melting point: 170° C.

EXAMPLE 14

4-Acetamido-N-(6-acetoxy-3,4-dihydro-2,5,7,8-tetramethyl-2H-1-benzopyran-2-carbonyl)benzene-sulfonamide The process is performed as in Method 1, using 4-acetamidobenzenesulfonamide as reagent.
Melting point: 182°–184° C.

EXAMPLE 15

4-Methyl-N-(6-acetoxy-2,5,7,8-tetramethyl-3,4-dihydro-2H-1-benzopyran-2-carbonyl)benzenesulfonamide
Method 3

To a solution of 3 g (10.25 mmol) of acetylated Trolox in 31 ml of anhydrous toluene are added 1.13 ml of thionyl chloride and three drops of dimethylformamide. The mixture is refluxed for three hours. It is allowed to cool and the solvent and the excess thionyl chloride are then evaporated off under vacuum. The acid chloride thus obtained is taken up in 10 ml of anhydrous THF.

1.76 g (10.25 mmol) of p-toluenesulfonamide are added slowly to a solution of 0.82 g (20.50 mmol) of 60% sodium hydride (prewashed with anhydrous toluene) in 15 ml of anhydrous THF. The acid chloride solution is poured gradually onto this mixture. The mixture is stirred at room temperature for 24 hours. The excess sodium hydride is destroyed with saturated aqueous sodium hydrogen carbonate solution. The aqueous phase is washed with dichloromethane and then acidified with 1M aqueous hydrochloric acid solution. The mixture is extracted with dichloromethane and the extracts are dried over anhydrous sodium sulfate. After removal of the solvent, the brown oil obtained is purified by chromatography on silica gel, eluting with a dichloromethane/ethanol mixture (99/1). After recrystallization from diisopropyl ether, 3.55 g of a white powder are collected.
Yield: 78%
m.p.: 127° C. (diisopropyl ether)
$C_{23}H_7NO_6S$
Mr: 445.54

EXAMPLE 16

4-tert-Butyl-N-(6-acetoxy-2,5,7,8-tetramethyl-3,4-dihydro-2H-1-benzopyran-2-carbonyl)benzenesulfonamide The process is performed as in Method 3, using 4-tert-butylbenzenesulfonamide as reagent instead of para-toluenesulfonamide.
Melting point: 125° C.

EXAMPLE 17

4-Methyl-N, N-(methyl)(6-acetoxy-3,4-dihydro-2,5,7,8-tetramethyl-2H-1-benzopyran-2-carbonyl)benzenesulfonamide The process is performed as in Method 3, using N-(methyl)-para-toluenesulfonamide as reagent instead of para-toluenesulfonamide.
Melting point: 132° C.

EXAMPLE 18

N-(3,4-Dihydro-6-hydroxy-2,5,7,8-tetramethyl-2H-1-benzopyran-2-carbonyl)methanesulfonamide
Method 4

To a solution of 1 g (2.7 mmol) of the derivative of Example 1 in 15 ml of ethanol are added 6.1 equivalents of aqueous 2M sodium hydroxide solution (16.5 mmol). The mixture is stirred under a stream of nitrogen for two hours. The mixture is diluted with water, acidified with aqueous 1M acetic acid solution and then extracted with dichloromethane. The organic phase is washed with water and dried over anhydrous sodium sulfate. The solvent is evaporated off and the residue is then recrystallized from diisopropyl ether in order to collect 0.71 g of a white powder.
Yield: 80%
m.p.: 185° C. (diisopropyl ether)
$C_{15}H_{21}NO_5S$
Mr: 327.40
IR (KBr), $v$ $cm^{-1}$: 3420 (vOH); 3375 (vNH); 1700 (vC=O amide); 1330 (vSO$_2$s); 1250 (comb NH/CN); 1175 (vSO$_2$as).

EXAMPLE 19

4-Fluoro-N-(3,4-dihydro-6-hydroxy-2,5,7,8-tetramethyl-2H-1-benzopyran-2-carbonyl)benzenesulfonamide The process is performed as in Method 4, using the compound of Example 2 as starting material.
Melting point: 139° C.

EXAMPLE 20

4-Chloro-N-(3,4-dihydro-6-hydroxy-2,5,7,8-tetramethyl-2H-1-benzopyran-2-carbonyl)benzenesulfonamide The process is performed as in Method 4, using the compound of Example 3 as starting material.
Melting point: 110° C.

EXAMPLE 21

4-Bromo-N-(3,4-dihydro-6-hydroxy-2,5,7,8-tetramethyl-2H-1-benzopyran-2-carbonyl)benzenesulfonamide The process is performed as in Method 4, using the compound of Example 4 as starting material.
Melting point: 115°–117° C.

EXAMPLE 22

4-Methyl-N-(3,4-dihydro-6-hydroxy-2,5,7,8-tetramethyl-2H-1-benzopyran-2-carbonyl)benzenesulfonamide The process is performed as in Method 4, using the compound of Example as starting material.
Melting point: 95° C.

EXAMPLE 23

4-tert-Butyl-N-(3,4-dihydro-6-hydroxy-2,5,7,8-tetramethyl-2H-1-benzopyran-2-carbonyl)benzene-sulfonamide The process is performed as in Method 4, using the compound of Example 16 as starting material.
Melting point: 122°–124° C.

EXAMPLE 24

N-(3,4-Dihydro-6-hydroxy-2,5,7,8-tetramethyl-2H-1-benzopyran-2-carbonyl)benzylsulfonamide The process is performed as in Method 4, using the compound of Example 6 as starting material.
Melting point: oil

EXAMPLE 25

N-(3,4-Dihydro-6-hydroxy-2,5,7,8-tetramethyl-2H-1-benzopyran-2-carbonyl)benzoic acid sulfonamide The process is performed as in Method 4, using the compound of Example 7 as starting material.
Melting point: 115°–117° C.

EXAMPLE 26

2-Nitro-N-(3,4-dihydro-6-hydroxy-2,5,7,8-tetramethyl-2H-1-benzopyran-2-carbonyl)benzenesulfonamide The process is performed as in Method 4, using the compound of Example 13 as starting material.
Melting point: 167°–169° C.

EXAMPLE 27

4-Fluoro-N-(3,4-dihydro-6-hydroxy-2,5,7,8-tetramethyl-2H-1-benzopyran-2-ylmethyl)benzenesulfonamide
Method 5

2 g (4.45 mmol) of the compound of Example 2 are dissolved in 150 ml of anhydrous diethyl ether. 0.84 g (22.25 mmol) of lithium aluminum hydride is added slowly and the mixture is then refluxed for 4 hours. After cooling, the excess hydride is destroyed by slow addition of ice-cold water. The mixture is filtered and the filtrate is extracted with dichloromethane, the organic phase is dried and the solvent is evaporated off. The product is purified on a column of silica, eluting with a dichloromethane/ethanol mixture (99/1). The product obtained is recrystallized from diisopropyl ether. 1.13 g of a white powder are recovered.
Yield: 65%
m.p.: 136°–138° C. (diisopropyl ether)
$C_{20}H_{24}FNO_4S$
Mr: 393.48
IR (KBr), $v$ $cm^{-1}$: 3450 (vOH); 3270 (vNH); 1580 (δNH); 1325 (vSO$_2$S); 1140 (vSO$_2$as).

EXAMPLE 28

4-Methyl-N-(3,4-dihydro-6-hydroxy-2,5,7,8-tetramethyl-2H-1-benzopyran-2-ylmethyl)benzenesulfonamide The process is performed as in Method 5, using the compound of Example 15 as starting material.
Melting point: 152°–154° C.

EXAMPLE 29

4-Chloro-N-(3,4-dihydro-6-hydroxy-2,5,7,8-tetramethyl-2H-1-benzopyran-2-ylmethyl)benzenesulfonamide The process is performed as in Method 5, using the compound of Example 3 as starting material.
Melting point: 135°–137° C.

EXAMPLE 30

4-Bromo-N-(3,4-dihydro-6-hydroxy-2,5,7,8-tetramethyl-2H-1-benzopyran-2-ylmethyl)benzenesulfonamide The process is performed as in Method 5, using the compound of Example 4 as starting material.
Melting point: 161° C.

EXAMPLE 31

N-(3,4-Dihydro-6-hydroxy-2,5,7,8-tetramethyl-2H-1-benzopyran-2-ylmethyl)methanesulfonamide The process is performed as in Method 5, using the compound of Example 1 as starting material.
Melting point: 125° C.

EXAMPLE 32

4-Bromo-N-(6-acetoxy-3,4-dihydro-2,5,7,8-tetramethyl-2H-1-benzopyran-2-ylmethyl)benzenesulfonamide
Method 6

10 g (39.95 mmol) of the derivative obtained in Example 30 are dissolved in 30 ml of anhydrous pyridine, the solution is cooled in an icebath and 18.8 ml of acetic anhydride are then added dropwise. The mixture is stirred for 2 hours at room temperature. The mixture is poured onto ice and the product is extracted with dichloromethane. The organic phase is washed with aqueous 1M hydrochloric acid solution, then with water and is dried over anhydrous sodium sulfate. After evaporation of the solvent, a solid residue is collected, which is recrystallized from diisopropyl ether in order to obtain 11 g of a white powder.
Yield: 94%
Melting point: 148° C. (diisopropyl ether)
$C_{23}H_{29}NO_5S$
Mr: 431.555
IR (KBr), ν cm$^{-1}$: 3304 (νNH); 1728 (νC=O); 1459 (δNH); 1331 (νSO$_2$s); 1159 (νSO$_2$as).

EXAMPLE 33

4-Methyl-N-(6-acetoxy-3,4-dihydro-2,5,7,8-tetramethyl-2H-1-benzopyran-2-ylmethyl)benzenesulfonamide The process is performed as in Method 6, using the compound of Example 28 as starting material.
Melting point: 130° C.

EXAMPLES 34 AND 35

6-Acetoxy-3,4-dihydro-2,5,7,8-tetramethyl-2H-1-benzopyran-2-carboxylic acid [2-(4-sulfamoylphenyl)-ethyl]amide (34)
4-(2-Aminoethyl)-N-(6-acetoxy-3,4-dihydro-2,5,7,8-tetramethyl-2H-1-benzopyran-2-carbonyl)benzenesulfonamide (35)
Method 7

5 g (17.1 mmol) of 6-acetoxy-3,4-dihydro-2,5,7,8-tetramethyl-2H-1-benzopyran-2-carboxylic acid are dissolved in anhydrous THF and 3.7 g (17.1 mmol) of carbonyldiimidazole are then added. The mixture is stirred at room temperature for 1 hour. 3.43 g (17.1 mmol) of 4-(2-aminoethyl)benzenesulfonamide are then added. The mixture is stirred overnight at room temperature. The solvent is evaporated off, the residue is taken up in dichloromethane and the solution is washed with water and dried over anhydrous sodium sulfate. The product is purified by chromatography on silica gel, eluting with dichloromethane gradually enriched with ethanol to 2.5%. 3 g of the compound of Example 35, then 7.6 g of the compound of Example 34 are collected, in this order. The compound of Example 34 is recrystallized from diisopropyl ether in order to obtain a white powder.

EXAMPLE 34

Yield: 94%
Melting point: 166° C. (diisopropyl ether)
$C_{24}H_{30}N_2O_6S$
Mr: 474.57
IR (KBr), ν cm$^{-1}$: 3420 (νNH): 1750 (νC=O ester); 1660 (νC=O amide); 1530 (δNH); 1370 (νSO$_2$s); 1150 (νSO$_2$s

EXAMPLE 35

Yield: 3.7%
Oil
$C_{24}H_{30}N_{2O}6S$
Mr: 474.57
IR (film), ν cm$^{-1}$: 3440 (νNH): 1750 (νC=O ester); 1690 (νC=O amide); 1530 (δNH); 1370 (νSO$_2$s); 1150 (νSO$_2$s)

EXAMPLE 36

6-Acetoxy-3,4-dihydro-2,5,7,8-tetramethyl-2H-1-benzopyran-2-carboxylic acid [2-(4-isocyanatosulfonylphenyl)ethyl]amide
Method 8

1 g (2.10 mmol) of the compound obtained in Example 34 is dissolved in 30 ml of anhydrous toluene with 0.2 ml (2.10 mmol) of oxalyl chloride, followed by addition of 0.4 ml( 2.4 mmol) of triethylamine. The mixture is stirred at room temperature for 5 hours. The toluene is evaporated off and the residue is chromatographed on neutral silica gel, eluting with dichloromethane. The product is recrystallized from diisopropyl ether.
0.36 g of an off-white product is thus obtained.
Yield: 34%
m.p.: 143° C.
$C_{25}H_{28}N_2O_7S$
Mr: 500.57
IR (KBr), ν cm$^{-1}$: 3430 (νNH): 1752 (νC=O ester); 1675 (νC=O amide); 1518 (δNH); 1371 (νSO$_2$s); 1174 (νSO$_2$as)

EXAMPLE 37

6-Acetoxy-3,4-dihydro-2,5,7,8-tetramethyl-2H-1-benzopyran-2-carboxylic acid {2-[4-(N'-[3-azabicyclo-[3.3.0]octyl])ureidosulfonylphenyl]ethyl}amide
Method 9

0.36 g (0.70 mmol) of the compound obtained in Example 36 is dissolved in a minimum amount of anhydrous dichloromethane, followed by dropwise addition of 0.1 ml (0.70 mmol) of N-aminoaza-3-bicyclo[3.3.0]octane until the isocyanate has disappeared on TLC. The solvent is evaporated off and the oily residue is chromatographed on neutral silica gel, eluting with ethyl acetate. 0.28 g of a yellow oil is thus obtained.
Yield: 62%
$C_{32}H_{42}N_4O_7S$
Mr: 626.78
IR (film, ν cm$^{-1}$: 3700–3250 (νNH amide and urea): 1754 (νC=O ester); 1666, 1664 (νC=O amide and urea); 1524 (δNH); 1369 (νSO$_2$s); 1163 (νSO$_2$as)

EXAMPLE 38

6-Acetoxy-3,4-dihydro-2,5,7,8-tetramethyl-2H-1-benzopyran-2-carboxylic acid {2-(4-(N'-[4-methyl-cyclohexyl])ureidosulfonylphenyl]ethyl}amide The process is performed as in Method 9, using 4-methylcyclohexylamine as reagent.
Yield: 70%
Oil
$C_{32}H_{43}N_3O_7S$
Mr: 613.78
IR (film, ν cm$^{-1}$: 3425–3283 (νNH amide and urea): 1755 (νC=O ester); 1668, 1666 (νC=O amide and urea); 1524 (δNH); 1369 (νSO$_2$s); 1161 (νSO$_2$as)

EXAMPLE 39

4-Chloro-N-(6-[(quinolin-2-yl)methoxy]-3,4-dihydro-2,5,7,8-tetramethyl-2H-1-benzopyran-2-carbonyl)benzenesulfonamide
Method 10
The process is performed as in Method 1, using 6-[(quinolin-2-yl)methoxy]-3,4-dihydro-2,5,7,8-tetramethyl-2H-1-benzopyran-2-carboxylic acid as substrate and the reagent of Example 3.
Melting point: 132°–134° C.

EXAMPLE 40

4-Fluoro-N-(6-[(quinolin-2-yl)methoxy]-3,4-dihydro-2,5,7,8-tetramethyl-2H-1-benzopyran-2-carbonyl)benzenesulfonamide
The process is performed as in Method 10, using the reagent of Example 2 instead of that of Example 3.
Melting point: 148° C.

EXAMPLE 41

N-(6-[(Quinolin-2-yl)methoxy]-3,4-dihydro-2,5,7,8-tetramethyl-2H-1-benzopyran-2-carbonyl)methanesulfonamide
The process is performed as in Method 10, using the reagent of Example 1 instead of the reagent of Example 3.
Melting point: 135° C.

EXAMPLE 42

4-Fluoro-N-(6-[(7-chloroquinolin-2-yl)methoxy]-3,4-dihydro-2,5,7,8-tetramethyl-2H-1-benzopyran-2-carbonyl) benzenesulfonamide
Method 11
The process is performed as in Method 1, using 6-[(7-chloroquinolin-2-yl)methoxy]-3,4-dihydro-2,5,7,8-tetramethyl-2H-1-benzopyran acid as substrate and the reagent of Example 2.
Melting point: 123°–125° C.

EXAMPLE 43

4-Chloro-N-(6-[(7-chloroquinolin-2-yl)methoxy]-3,4-dihydro-2,5,7,8-tetramethyl-2H-1-benzopyran-2-carbonyl)benzenesulfonamide
The process is performed as in Method 11, using the reagent of Example 3 instead of the reagent of Example 2.
Melting point: 141°–143° C.

EXAMPLE 44

4-Bromo-N-(6-methoxy-3,4-dihydro-2,5,7,8-tetramethyl-2H-1-benzopyran-2-carbonyl)benzenesulfonamide
The process is performed as in Method 1, using 6-methoxy-3,4-dihydro-2,5,7,8-tetramethyl-2H-1-benzopyran-2-carboxylic acid as starting material and the reagent of Example 4.
Melting point: 134°–136° C.

EXAMPLE 45

4-Acetamido-N-(6-acetoxy-3,4-dihydro-2,5,7,8-tetramethyl-2H-1-benzopyran-2-ylmethyl)benzenesulfonamide
The process is performed as in Method 5, using the compound of Example 14 as starting material, which is treated in a second step according to Method 6.
Melting point: 95° C.

EXAMPLE 46

4-Methyl-N-(6-acetoxy-3,4-dihydro-2-methyl-7-tert-butyl-2H-1-benzopyran-2-carbonyl)benzenesulfonamide
The process is performed as in Method 3, using 6-acetoxy-3,4-dihydro-2-methyl-7-tert-butyl-2H-1-benzopyran-2-carboxylic acid as starting material.
Melting point: 67° C.

EXAMPLE 47

4-Methyl-N-(6-methoxy-3,4-dihydro-2,5,7,8-tetramethyl-2H-1-benzopyran-2-carbonyl)benzenesulfonamide
The process is performed as in Method 3, using 6-methoxy-3,4-dihydro-2,5,7,8-tetramethyl-2H-1-benzopyran-2-carboxylic acid as starting material.
Melting point: 130° C.

EXAMPLE 48

4-Methyl-N-(6-isobutyryloxy-3,4-dihydro-2,5,7,8-tetramethyl-2H-1-benzopyran-2-carbonyl)benzenesulfonamide
The process is performed as in Method 3, using 6-isobutyryloxy-3,4-dihydro-2,5,7,8-tetramethyl-2H-1-benzopyran-2-carboxylic acid as starting material.
Melting point: 103°–104° C.

EXAMPLE 49

4-Bromo-N-(6-isobutyryloxy-3,4-dihydro-2,5,7,8-tetramethyl-2H-1-benzopyran-2-carbonyl)benzenesulfonamide
The process is performed as in Method 1, using the starting material of Example 48 as starting material.
Melting point: 97°–103° C.

EXAMPLE 50

4-Bromo-N-(6-n-butyryloxy-3,4-dihydro-2,5,7,8-tetramethyl-2H-1-benzopyran-2-carbonyl)benzenesulfonamide
The process is performed as in Method 1, using 6-n-butyryloxy-3,4-dihydro-2,5,7,8-tetramethyl-2H-1-benzopyran-2-carboxylic acid as substrate.
Melting point: 139°–142° C.

EXAMPLE 51

4-Methyl-N-(6-acetoxy-3,4-dihydro-2,5,7,8-tetramethyl-2H-1-benzopyran-2-carbonyl)benzenesulfonamide
The process is performed as in Method 1 of Example 1, using 4-methoxybenzenesulfonamide as reagent.
Melting point: 144° C.

EXAMPLE 52

4-Methyl-N-(6-tert-pentryloxy-3,4-dihydro-2,5,7,8-tetramethyl-2H-1-benzopyran-2-carbonyl)benzenesulfonamide
The process is performed as in Method 3, using 6-tert-pentryloxy-3,4-dihydro-2,5,7,8-tetramethyl-2H-1-benzopyran-2-carboxylic acid as starting material.
Melting point: 97° C.

EXAMPLE 53

4-Bromo-N-(6-tert-pentryloxy-3,4-dihydro-2,5,7,8-tetramethyl-2H-1-benzopyran-2-carbonyl)benzenesulfonamide The process is performed as in Method 1, using the substrate of Example 52 and the reagent of Example 4.
Melting point: 125° C.

EXAMPLE 54

4-Methyl-N-(6-n-butyryloxy-3,4-dihydro-2,5,7,8-tetramethyl-2H-1-benzopyran-2-carbonyl)benzenesulfonamide The process is performed as in Method 3, using the substrate of Example 50.
Melting point: 103° C.

EXAMPLE 55

4-Acetamido-N-(6-tert-pentyryloxy-3,4-dihydro-2,5,7,8-tetramethyl-2H-1-benzopyran-2-ylmethyl)benzenesulfonamide The process is performed as in Method 5, and then as in Method 6.
Melting point: 51° C.

EXAMPLE 56

4-Methyl-N-(6-propyryloxy-3,4-dihydro-2,5,7,8-tetramethyl-2H-1-benzopyran-2-carbonyl)benzenesulfonamide The process is performed as in Method 3, using 6-propyryloxy-3,4-dihydro-2,5,7,8-tetramethyl-2H-1-benzopyran-2-carboxylic acid as starting material.
Melting point: 98° C.

EXAMPLE 57

4-Bromo-N-(6-propyryloxy-3,4-dihydro-2,5,7,8-tetramethyl-2H-1-benzopyran-2-carbonyl)benzenesulfonamide The process is performed as in Method 1, using the substrate of Example 56 and the reagent of Example 4.

EXAMPLE 58

6-Hydroxy-3,4-dihydro-2,5,7,8-tetramethyl-2H-1-benzopyran-2-carboxylic acid [2-(4-sulfamoylphenyl)-ethyl]amide The process is performed as in Method 4, using the compound of Example 34 as substrate.
Melting point: 184° C.

EXAMPLE 59

N-{4-[2-(5-Methylpyrazine-2-carboxamido)ethyl]benzenesulfonyl}-(6-acetoxy-3,4-dihydro-2,5,7,8-tetramethyl-2H-1-benzopyran-2-yl)-carboxamide The process is performed as in Method 3, using 4-[2-(5-methylpyrazine-2-carboxamido)ethyl]benzenesulfonamide as reagent.
Melting point: 156°–158° C.

EXAMPLE 60

N-{4-[2-(5-Methylpyrazine-2-carboxamido)ethyl]benzenesulfonyl]-(6-propyryloxy-3,4-dihydro-2,5,7,8-tetramethyl-2H-1-benzopyran-2-yl)carboxamide The process is performed as in Method 3, using the substrate of Example 56 and the reagent of Example 59.
Melting point: 112° C.

EXAMPLE 61

N-{4-[2-(5-Methylpyrazine-2-carboxamido)ethyl]benzenesulfonyl}-(6-tert-pentyryloxy-3,4-dihydro-2,5,7,8-tetramethyl-2H-1-benzopyran-2-yl)carboxamide The process is performed as in Method 3, using the substrate of Example 52 and the reagent of Example 59.
Melting point: 85°–90° C.

EXAMPLE 62

6-Acetoxy-3,4-dihydro-2,5,7,8-tetramethyl-2H-1-benzopyran-2-carboxylic acid (2-[4-(N'-[4-methylcyclohexyl]ureidosulfonylphenyl]methyl}amide The process is performed as in Method 7, using 4-(2-aminomethyl) benzenesulfonamide as reagent, followed by treatment according to Method 8 and then Method 9, using in this final step the reagent used in Example 38.
Melting point: 90° C.

EXAMPLE 63

4-Phthalimidomethyl-N-(6-acetoxy-3,4-dihydro-2,5,7,8-tetramethyl-2H-1-benzopyran-2-carbonyl)benzenesulfonamide The process is performed as in Method 3, using 4-phthalimidomethylbenzenesulfonamide as reagent.
Melting point: 90° C.

EXAMPLE 64

4-[2-Phthalimidoethyl)-N-(6-acetoxy-3,4-dihydro-2,5,7,8-tetramethyl-2H-1-benzopyran-2-carbonyl)benzenesulfonamide The process is performed as in Method 3, using 4-(2-phthalimidoethyl) benzenesulfonamide as reagent.
Melting point: 150° C.

PHARMACOLOGICAL STUDY

A. Investigation of Antidiabetic Activity

Animals and treatments:

Three-month-old male Wistar rats weighing approximately 250 g were used for all the experiments.

The animals are kept in a room at a temperature of 21±2° C. with alternating day/night periods 12 hours in duration. They are given free access to food and water. An experimental diabetes is obtained by iv injection of a low dose of streptozotocine dissolved in citrate buffer under anesthesia with ketamine hydrochloride (75 mg/kg, IP). These rats are referred to as the "STZ rats". The normal rats received an injection of citrate buffer under the same conditions.

Carbohydrate homeostasis was evaluated by a test of tolerance to glucose, performed two weeks after injection of streptozotocine.

Glucose tolerance test:

IVGTT (intravenous glucose tolerance test)

The glucose is dissolved in aqueous 0.9% NaCl solution and administered via the saphene vein to rats anesthetized with pentobarbital (60 mg/kg, IP). Blood samples are collected sequentially by the blood vessels in the tail before injection and 5, 10, 15, 20 and 30 minutes after injection of glucose. They are then centrifuged and the plasma is separated. The plasmatic glucose concentration is determined immediately on an aliquot of 10 µl and the remaining plasma is stored at −20° C.

OGTT (oral glucose tolerance test)

Glucose is administered orally (2 g/kg) to conscious rats. Blood samples are collected before and 10, 20, 30, 40, 90 and 120 minutes after administration of glucose. The treatment of the blood samples is identical to that described above.

Administration of the test products

The rats anesthetized with pentobarbital receive a single IP injection of the test product 20 minutes before the IVGTT. The product is administered orally 30 minutes before the OGTT.

Products used ketamine hydrochloride (Imalgene, Mérieux)

pentobarbital (Clin-Midy)

Effect of the product on basal qlycemia:

A single administration of the test product is made orally to rats in the post-prandial period. Blood samples are collected via the vessels in the tail, before and every 30 minutes for 3 hours after administration of the product. The level of plasmatic glucose is measured immediately.

Analytical methods:

The plasmatic glucose concentration is determined using a glucose analyzer (Beckman Inc., Fullerton, Calif.). The glucose tolerance is measured relative to two parameters: ΔG and K.

ΔG represents the increase in glycemia above the base line, integrated on a base of 30 minutes (IVGTT) or of 120 minutes (OGTT), after glucose overload.

K is the rate of disappearance of the glucose between 5 and 30 minutes (IVGTT), after administration of glucose. The coefficient K is calculated only during the IVGTT.

The products of the invention have good activity in these predictive tests of use in the treatment of diabetes.

B. Study of the Antiperoxidizing Activity

The ability of the compounds of the invention to trap OH radicals was studied, on the one hand, on the spontaneous peroxidation of lipids and, on the other hand, on the peroxidation induced by the $Fe^{2+}$-ascorbate system ($10 \mu M$–$250 \mu M$), carried out on rat brain homogenates.

During measurement of the spontaneous lipid peroxidation, the rat brain homogenates are placed in the presence or absence of the test compounds for 60 minutes at 37° C. The reaction is stopped at 0° C. and the malondialdehyde is assayed using thiobarbituric acid by the method of Yagi, K (1976) Biochem. Med, 15, 212–216. The lipid peroxidation is determined by substances which react with thiobarbituric acid, expressed in nanomoles of malondialdehyde.

During measurement of the induced lipid peroxidation, the methodology is identical to that above, except for the addition of the radical-inducing system: Fe 2+-ascorbate, to the homogenate. The reference substances are probucol and vitamin E.

The concentrations of the test compounds which inhibit the peroxidation of the substrate by 50% are calculated.

It was seen that certain compounds of the invention have a particularly intense antiperoxidizing activity. This very advantageous result occurs whether the peroxidation is spontaneous or induced by a chemical system.

C. Study of the Protective Power on the Oxidation of LDLs

The capacity of the compounds of the invention to decrease the proportions of LDL was measured in the following way. An incubation was carried out for 24 hours combining native LDLs, a free-radical-generating $Cu^{2+}$ system and the test compounds.

The results are obtained after analyzing the medium by a high performance chromatographic technique: FPLC (Fast Protein Liquid Chromatography). The protective power of the test compound is determined after comparison of the chromatogram obtained with that of the positive reference control: probucol.

It is seen clearly that the compounds of the invention have a very high protective power which is significantly higher than that of the reference compound. The activity of the product of the invention on these two tests also makes it possible to envisage an advantageous activity on the side effects of diabetic disease.

ACUTE TOXICITY

The acute toxicity was evaluated after oral administration of a dose of 650 mg/kg to batches of eight mice (26±2 grams). The animals were observed at regular intervals during the first day and daily for the two weeks following the treatment.

It is seen that most of the compounds of the invention are completely nontoxic. Most of them cause no death after administration of a dose of 650 mg/kg and, in general, no disorders are observed after administration of this dose.

PHARMACEUTICAL COMPOSITIONS:

Tablets intended for treating diabetes or side effects of diabetic disease, containing a 50 mg dose of 4-methyl-N-(6-acetoxy-3,4-dihydro-2,5,7,8-tetramethyl-2H-1-benzopyran-2-carbonyl)benzenesulfonamide.

Preparation formula for 1000 tablets:

| | |
|---|---|
| 4-methyl-N-(6-acetoxy-3,4-dihydro-2,5,7,8-tetramethyl-2H-1-benzopyran-2-carbonyl) benzenesulfonamide | 50 g |
| Wheat starch | 50 g |
| Cornstarch | 50 g |
| Lactose | 175 g |
| Magnesium stearate | 5 g |
| Silica | 2.5 g |
| Hydroxypropylcellulose | 5 g |

We claim:

1. A compound selected from those of formula (I):

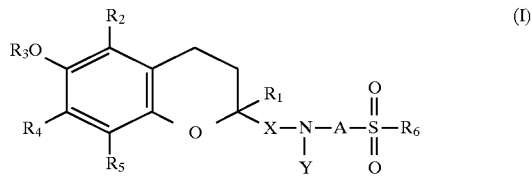

in which:

$R_1$ represents linear or branched ($C_1$–$C_9$) alkyl;

$R_2$, $R_4$ and $R_5$, which may be identical or different, each represent, independently of each other, hydrogen or linear or branched ($C_1$–$C_9$) alkyl;

$R_3$ represents hydrogen, linear or branched ($C_1$–$C_9$) alkyl, linear or branched ($C_1$–$C_9$) acyl, linear or branched carboxy ($C_1$–$C_9$) alkyl, linear or branched ($C_1$–$C_9$) alkoxycarbonyl, or

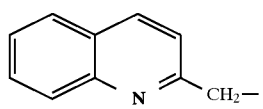

which is optionally substituted with halogen in position 7;

X represents carbonyl or methylene;

Y represents hydrogen, linear or branched ($C_1$–$C_9$) alkyl or optionally substituted aryl;

A represents either single bond and, in this case:

$R_6$ represents linear or branched ($C_1$–$C_9$) alkyl (optionally substituted with aryl which is itself optionally substituted), or optionally substituted aryl;

or alkylphenyl (optionally substituted on the phenyl) —$R_b$—Ph, linear or branched ($C_1$–$C_9$) alkyl part Rb being attached to $$-\underset{\underset{Y}{|}}{N}-$$

and, in this case:
$R_6$ represents:
isocyano,
amino optionally substituted with one or two identical or different, linear or branched ($C_1$–$C_9$) alkyl, or with linear or branched ($C_1$–$C_9$) alkoxycarbonyl,
or substituted urea —NH—CO—NH—$R_7$ with $R_7$ representing phenyl (optionally substituted), cyclo ($C_5$–$C_8$) alkyl (optionally substituted with linear or branched ($C_1$–$C_9$) alkyl), or 3-azabicyclo[3.3.0]octyl, the term aryl being understood to refer to a phenyl or naphthyl and the term substituted aryl or substituted phenyl being understood to refer to aryl or phenyl having 1 to 3 substitutions, which may be identical or different, chosen, independently of each other, from:

linear or branched ($C_1$–$C_9$) alkyl,
linear or branched ($C_1$–$C_9$) alkoxy,
linear or branched ($C_1$–$C_9$) alkoxycarbonyl,
carboxyl,
linear or branched carboxy ($C_1$–$C_9$) alkyl,
linear or branched ($C_1$–$C_9$) acyl,
linear or branched ($C_1$–$C_9$) alkylcarbonylamino,
linear or branched ($C_1$–$C_9$) aminoalkyl, $$(CH_2)_n-NH-CO-\underset{\underset{N}{\diagdown\diagup}}{\overset{\overset{N}{\diagup\diagdown}}{}}-$$

where n is 1 and 6 inclusive,
amino optionally substituted with one or two identical or different, linear or branched ($C_1$–$C_9$) alkyl,
linear or branched ($C_1$–$C_9$) alkenyl,
nitro,
halo,
trihalomethyl,
linear or branched phthalimido ($C_1$–$C_9$) alkyl, its optical isomers as well as its addition salts with a pharmaceutically acceptable acid or base.

2. The compound of formula (I) as claimed in claim 1, wherein:

$R_1$, $R_2$, $R_4$ and $R_5$, which may be identical or different, represent linear or branched ($C_1$–$C_9$) alkyl,
$R_3$ represents hydrogen or linear or branched ($C_1$–$C_9$) acyl,
X represents carbonyl, Y represents hydrogen or linear or branched ($C_1$–$C_9$) alkyl, A represents
a single bond and, in this case, $R_6$ represents optionally substituted aryl,
or phenylethyl and, in this case, $R_6$ represents substituted urea —NH—CO—NH—$R_7$ in which $R_7$ represents phenyl (optionally substituted), cyclo ($C_5$–$C_8$) alkyl optionally substituted with linear or branched ($C_1$–$C_9$) alkyl, or 3-azabicyclo[3.3.0]octyl, its optical isomers as well as its addition salts with pharmaceutically acceptable acid or base.

3. A compound of claim 1, wherein:
A represents a single bond and $R_6$ represents phenyl substituted with linear or branched ($C_1$–$C_9$) alkyl, halogen, or $$(CH_2)_n-NH-CO-\underset{\underset{N}{\diagdown\diagup}}{\overset{\overset{N}{\diagup\diagdown}}{}}-$$

where n is 1 to 6 inclusive,
its optical isomers as well as its addition salts thereof with a pharmaceutically acceptable acid or base.

4. A compound of claim 1, which is selected from 4-chloro-N-(6-acetoxy-3,4-dihydro-2,5,7,8-tetramethyl-2H-1-benzopyran-2-carbonyl)-benzenesulfonamide and its salts with a pharmaceutically acceptable acid or base.

5. The compound of claim 1, which is selected from 4-bromo-N-(6-acetoxy-3,4-dihydro-2,5,7,8-tetramethyl-2H-1-benzopyran-2-carbonyl)-benzenesulfonamide, and its salts with a pharmaceutically acceptable acid or base.

6. A compound of claim 1, which is selected from 4-methyl-N-(6-acetoxy-3,4-dihydro-2,5,7,8-tetramethyl-2H-1-benzopyran-2-carbonyl)-benzenesulfonamide, and its salts with a pharmaceutically acceptable acid or base.

7. A method for treating a living body, afflicted with a condition selected from diabetes and complications of diabetic disease, comprising the step of administering to the living body an amount of a compound of claim 1 which is effective for alleviation of said condition.

8. A pharmaceutical composition useful in treating diabetes comprising as active principle an effective amount of a compound of claim 1, together with one or more pharmaceutically acceptable excipients or vehicles.

9. A compound of claim 2, wherein A represents a single bond and $R_6$ represents phenyl substituted with linear or branched ($C_1$–$C_9$) alkyl, halogen, or $$(CH_2)_n-NH-CO-\underset{\underset{N}{\diagdown\diagup}}{\overset{\overset{N}{\diagup\diagdown}}{}}-$$

where n is 1 to 6 inclusive, its optical isomers as well as addition salts thereof with a pharmaceutically-acceptable acid or base.

10. A compound of claim 2, wherein Y represents hydrogen.

* * * * *

UNITED STATES PATENT AND TRADEMARK OFFICE
CERTIFICATE OF CORRECTION

PATENT NO. : 5,889,045
DATED : Mar. 30, 1999
INVENTOR(S) : T. Muller, C. Moulin, M. Duflos, S. Robert-Pissard, G. LeBaut, A. Tonnerre, D-H. Caignard, D. Manechez, P. Renard Page 1 of 4

It is certified that error appears in the above-indentified patent and that said Letters Patent is hereby corrected as shown below:

Column 7, line 54: "carbonyidiimidazole" should read -- carbonyldiimidazole --.

Column 10, line 6: "Example as" should read -- Example 15 as --.

Column 10, line 59: "($vSO_2S$);" should read -- ($vSO_2S$); --.

Column 12, line 16: At the end of the line, insert -- ) --.

Column 12, line 20: "$C_{24}H_{30}N_{206}S$" should read -- $C_{24}H_{30}N_2O_6S$ --.

Column 12, line 31: Delete the "(" at the end of the line.

Column 12, line 32: At the beginning of the line, insert -- ( --.

Column 13, line 15: At the end of the line, delete the "[".

Column 13, line 16: At the beginning of the line, insert -- [ --.

Column 17, line 47: "Fe 2+-ascorbate," should read -- $Fe^{2+}$-ascorbate, --.

UNITED STATES PATENT AND TRADEMARK OFFICE
CERTIFICATE OF CORRECTION

PATENT NO. : 5,889,045
DATED : Mar. 30, 1999
INVENTOR(S) : T. Muller, C. Moulin, M. Duflos, S. Robert-Pissard, G. LeBaut, A. Tonnerre, D-H. Caignard, D. Manechez, P. Renard It is certified that error appears in the above-indentified patent and that said Letters Patent is hereby corrected as shown below:

Column 18, line 64: Insert a --,-- (comma) after the word "alkyl".

Column 18, line 67: Insert -- a -- between "either" and "single".

Column 19, line 6: "-R$_b$-Ph," should read -- -Rb-Ph, --.

Column 19, line 46: The word "and" between the numbers "1" and "6" should read -- to --.

Column 19, line 56: Insert a -- - -- (hyphen) between "pharmaceutically" and "acceptable".

Column 19, line 57: At the beginning of the line, "The" should read -- A --, and "formula (I) as claimed in" should be "of".

Column 20, line 11: Insert the word -- a -- before "pharmaceutically" and insert -- - -- (hyphen) between "pharmaceutically" and "acceptable".

UNITED STATES PATENT AND TRADEMARK OFFICE
CERTIFICATE OF CORRECTION

PATENT NO. : 5,889,045
DATED : Mar. 30, 1999                                Page 3 of 4
INVENTOR(S) : T. Muller, C. Moulin, M. Duflos,
S.Robert-Pissard, G. LeBaut, A. Tonnerre,
D-H. Caignard, D. Manechez, P. Renard It is certified that error appears in the above-indentified patent and that said Letters Patent is hereby corrected as shown below:

Column 20, line 25: Delete "its" before "addition".

Column 20, line 26: Insert a -- - -- (hyphen) between "pharmaceutically" and "acceptable".

Column 20, line 30: Insert a -- - -- (hyphen) between "pharmaceutically" and "acceptable".

Column 20, line 31" "The" at the beginning of the line should read -- A --.

Column 20, line 33: Delete the "," (comma) after "benzenesulfonamide".

Column 20, line 34: Insert a -- - -- (hyphen) between "pharmaceutically" and "acceptable".

Column 20, line 37: Delete the "," (comma) after the word "benzenesulfonamide".

UNITED STATES PATENT AND TRADEMARK OFFICE
CERTIFICATE OF CORRECTION

PATENT NO. : 5,889,045
DATED : Mar. 30, 1999
INVENTOR(S) : T. Muller, C. Moulin, M. Duflos, S. Robert-Pissard, G. LeBaut, A. Tonnerre, D-H. Caignard, D. Manechez, P. Renard It is certified that error appears in the above-indentified patent and that said Letters Patent is hereby corrected as shown below:

Column 20, line 38: Insert a -- - -- (hyphen) between "pharmaceutically" and "acceptable".

Column 20, line 47: Insert a -- - -- (hyphen) between "pharmaceutically" and "acceptable".

Signed and Sealed this

Thirty-first Day of August, 1999

Attest:

Q. TODD DICKINSON

Attesting Officer

Acting Commissioner of Patents and Trademarks